US006281337B1

(12) United States Patent
Cannon-Carlson et al.

(10) Patent No.: US 6,281,337 B1
(45) Date of Patent: Aug. 28, 2001

(54) METHODS FOR CONVERSION OF PROTEIN ISOFORMS

(75) Inventors: Susan Cannon-Carlson, Wayne; Andres Frei, Freehold; Seoju Lee, Edison; Roland Mengisen, Freehold, all of NJ (US); Marcio Voloch, New York City, NY (US); David C. Wylie, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/441,653

(22) Filed: Nov. 12, 1999

Related U.S. Application Data
(60) Provisional application No. 60/107,978, filed on Nov. 12, 1998.

(51) Int. Cl.$^7$ .............................. C07K 1/00; C07K 14/00; C07K 16/00; C07K 17/00; A61K 35/14
(52) U.S. Cl. ................. 530/402; 530/350; 530/351; 530/380; 530/412; 530/427
(58) Field of Search .................................. 530/350, 351, 530/380, 412, 402, 427

(56) References Cited

U.S. PATENT DOCUMENTS

| | | | |
|---|---|---|---|
| 4,315,852 | 2/1982 | Leibowitz et al. | 260/112 |
| 4,364,863 | 12/1982 | Leibowitz et al. | 260/112 |
| 4,496,537 | 1/1985 | Kwan | 424/85 |
| 4,530,901 | 7/1985 | Weissmann | 435/70 |
| 4,732,683 | 3/1988 | Georgiades et al. | 210/635 |
| 4,765,903 | 8/1988 | D'Andrea et al. | 210/635 |
| 4,847,079 | 7/1989 | Kwan | 424/85 |
| 5,272,135 | 12/1993 | Takruri | 514/12 |
| 5,460,956 | 10/1995 | Reichert et al. | 435/69.51 |
| 5,766,582 | 6/1998 | Yuen et al. | 424/85.7 |

FOREIGN PATENT DOCUMENTS

| | | | |
|---|---|---|---|
| 0 032 134 | 7/1981 | (EP) | C12N/15/00 |
| 0 108 585 | 5/1984 | (EP) | C12P/21/02 |

OTHER PUBLICATIONS

Gansow et al., "Detection and Identification of Intermediates and Products of a Nonenzymatic Transamination Reaction by Proton Resonance," Journal of the American Chemical Society, 90:20, (Sep. 25, 1968) 5629–30.

Darwish et al., "The Racemization of Sulfonium Salts. II. The Racemization of Substituted Benzylethylmethylsulfonium Perchlorates," Journal of the American Chemical Society, 90:20 Sep. 25, 1968.

Victor J. Stevens, et al., "Nonenzymatic Glycosylation of Hemoglobin," The Journal of Biological Chemistry, vol. 252, No. 9, Issue of May 10, pp. 2998–3002, 1977.

Victor G. Edy, et al., "Purification of Human Fibroblast Interferon by Zinc Chelate Affinity Chromatography," The Journal of Biological Chemistry vol. 252, No. 17, Issue of Sep. 10, pp. 5934–5935, 1977.

Robert Shapiro, et al., "Sites of Nonenzymatic Glycosylation of Human Hemoglobin A," The Journal of Biological Chemistry, vol. 255, No. 7, Issue of Apr. 10, pp. 3120–3127, 1980.

J. W. Heine, et al., "Purification of Human Fibroblast Interferon by Zinc Chelate Chromatography," J. Gen. Virol. 54:47–56, 1981.

Menachem Rubinstein, "The Structure of Human Interferons," Biochimica et Biophysica Acta, 695 (1982) 5–16.

Jun Utsumi, et al., "Elimination of contaminating *Escherichia coli* peptides in the purification of *Escherichia coli*–derived recombinant human interferon–β1 by Zinc Chelate Affinity Chromatography," Journal of Chromatography, 490 (1989) 193–197.

Danielle Prome, et al., "Structure of the Human Adult Hemoglobin Minor Fraction $A_{1b}$ by Electrospray and Secondary Ion Mass Spectrometry," The Journal of Biological Chemistry, vol. 266, No. 20, Issue of Jul. 15, pp. 13050–13054, 1991.

Keith Rose, et al., "Pyruvic Acid is Attached through Its Central Carbon Atom to the Amino Terminus of the Recombinant DNA–derived DNA–binding Protein Ner of Bacteriohage Mut," The Journal of Biological Chemistry, vol. 26, No. 27, Issue of Sep. 25, pp. 19101–19106, 1992.

Xanthe M. Lam, Journal of Pharmaceutical Sciences, vol. 86, No. 11, Nov. 1997, Abstract.

Irem Cakman, et al., "Zinc Supplementation Reconstitutes the Production of Interferon–α by Leukocytes from Elderly Persons," Journal of Interferon and Cytokine Research, 17:469–472 (1997).

*Primary Examiner*—Elizabeth Kemmerer
*Assistant Examiner*—Robert S. Landsman
(74) *Attorney, Agent, or Firm*—Donald W. Wyatt

(57) ABSTRACT

The present invention provides methods for isolating adjunct isoforms of proteins and converting them to the desired protein. In preferred embodiments, the present invention contemplates the use of acid solutions or zinc solutions to cleave a chemical group from a desired protein. In further preferred embodiments, the present invention contemplates the oxidation of reduced sulfhydryl groups with cleavage of chemical groups to form a functional desired protein.

17 Claims, No Drawings

METHODS FOR CONVERSION OF PROTEIN ISOFORMS

This application claims the benefit of U.S. provisional patent application Ser. No. 60/107,978 filed Nov. 12, 1998. Throughout this disclosure, various publications, patents and patent applications are referenced. The disclosures of these publications, patents and patent applications are herein incorporated by reference.

FIELD OF THE INVENTION

The present invention pertains to the isolation and purification of proteins. In particular, the present invention pertains to the isolation of proteins, isolation of isoforms of proteins and conversion of isoforms to the desired proteins.

BACKGROUND

Naturally occurring proteins are widely used for research and clinical purposes. While such proteins may be obtained from their natural source, recombinant techniques can permit the production of these proteins from non-natural sources. For example, fermentation of microorganisms constructed via recombinant technology, such as transformed bacteria, produce large quantities of human interferon at a substantially lower cost than is possible utilizing natural sources. Such recombinant DNA techniques have also been utilized to produce other important proteins, such as insulin and tissue plasminogen activator.

Bacteria altered by recombinant techniques, however, also produce contaminants and structural isoforms of the protein intended to be produced. These contaminants and isoforms include oligomeric proteins and reduced protein isoforms (see U.S. Pat. No. 4,765,903 to D'Andrea et al.), cell debris and viruses (see U.S. Pat. No. 4,732,683 to Georgiadis et al.) and pyruvate-linked isoforms (see Rose et al., J. Biol. Chem. 287:19101 (1992); Prome et al, J. Biol. Chem. 266:13050 (1991); Stevens et al, J. Biol. Chem. 252:2998 (1977); and Shapiro et al, J. Biol. Chem. 255:3120 (1980)). It is desirable to remove these contaminants during purification of the protein.

Clearly, these protein isoforms reduce the purity of the desired protein and the processes for removal of the isoforms reduce the overall yield. If, however, the protein isoforms can be converted to the desired protein, their removal is unnecessary and the overall protein yields would be significantly increased. What is needed is a way to identify undesired protein isoforms and convert them to the desired protein. The present invention addresses such needs.

SUMMARY OF THE INVENTION

The present invention provides methods for preparing highly purified proteins in high yields by isolating adjunct isoforms and converting them to a desired, functional protein. In one embodiment, the present invention provides a method for increasing the yield of an interferon alpha composition, comprising converting an adjunct isoform into interferon alpha. While the present invention is not limited to a particular interferon alpha, in a preferred embodiment the interferon alpha is interferon alpha2b.

In another embodiment, the present invention provides methods for converting a recombinantly produced adjunct isoform to the desired protein comprising chemically removing a cleavable group from the adjunct isoform.

The present invention is not limited by the cleavable group removed. In one embodiment the cleavable group comprises pyruvate.

The present invention is also not limited by the method of chemically removing the cleavable group. In one embodiment, the method comprises exposing the adjunct isoform to acid solution. When the adjunct isoform is a pyruvate adjunct isoform of interferon alpha, it is preferred that the acid solution be at about pH 5.5. In such an embodiment, it is further preferred that the acid solution be at 34–40° C. In another embodiment, however, the adjunct isoform is exposed to a zinc solution. In a preferred embodiment, the zinc solution is at pH 7.8 to pH 8.6. In a further preferred embodiment, the zinc solution is at 30–38° C.

The present invention is also not limited by the type of acid or zinc solution utilized. In preferred embodiments, the acid solution or zinc solution comprise an antioxidant. In particularly preferred embodiments, the antioxidant comprises methionine. In such an embodiment, the preferred concentration of methionine is 5–40 mM.

Definitions

As used herein, the term "desired protein" means a protein of interest that is intended to be purified. The identification of the desired protein is, of course, subject to the ultimate goal of the purification procedure. For example, during a purification procedure it may be desirable to obtain a protein group or groups, including contaminants, in an intermediate step of the purification process. Regardless of the interest in obtaining an intermediate protein group, the protein group that is the ultimate goal of the purification procedure is considered the desired protein.

As used herein, the term "adjunct isoform" means a protein isoform having structural and/or functional characteristics similar to a desired protein, wherein a cleavable group can be removed from the protein to produce the desired protein. A "cleavable group" is understood to mean a chemical group attached to a desired protein that can be chemically removed. "Chemical removal" or "chemically removed" as used herein is understood to designate that a chemical group has been separated from a protein by chemical means, including, but not limited to, acidic solution, basic solutions, metal ion catalysis, etc.

While not being necessary to practice the present invention, if the cleavable group can be chemically identified, the adjunct isoform can be referred to as a specific type of adjunct isoform. For example, a "pyruvate adjunct isoform" is a desired protein having a cleavable group attached that is identifiable as pyruvate.

As used herein, the term "oxidation reaction" means a reaction intended to cause the sulfhydryl groups of two cysteine amino acids to form disulfide bonds.

As used herein, the term "interferon alpha" refers to a family of inducible secreted proteins that confer resistance to viruses on target cells, inhibit cell proliferation and regulate expression of MHC class I antigens. This family includes, but is not limited to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany) or consensus interferon as defined by determination of a consensus sequence of naturally occurring interferon alphas (Infergen, Amgen, Thousand Oaks, Calif.).

DETAILED DESCRIPTION OF THE INVENTION

The present invention pertains to the isolation and purification of proteins. In one embodiment, the present invention provides for the identification and purification of adjunct isoforms. In another embodiment, the present invention provides methods for producing a desired protein from adjunct isoforms. In yet another embodiment, the present invention provides a highly purified desired protein by the co-purification of the desired protein together with adjunct isoforms and the subsequent conversion of the adjunct isoforms to the desired protein. In this manner, the amount of the adjunct isoform is reduced and the overall yield of the desired protein is increased and/or is more highly purified than previously achievable. The yield of the desired protein can be increased by as much as ten times the yield as obtained without converting adjunct isoforms.

While the present invention is not limited by the source of the desired protein or the adjunct isoforms, in one embodiment, the source is microorganisms constructed via recombinant techniques. There are many such techniques known to those skilled in the art. Such transformed microorganisms may be eukaryotic or prokaryotic cells, bacteria, mammalian cells, etc. For example, interferon alpha may be produced in bacteria by following the teachings of U.S. Pat. No. 4,530,901 to Weissman or by the techniques described in European Patent Application publication number EP032,134.

Likewise, the present invention is not limited to any particular method of extracting the adjunct isoform from the producing cell. When the desired protein is interferon alpha, for example, the methods described in U.S. Pat. Nos. 4,315,852 and 4,364,863 to Leibowitz et al, are suitable.

Likewise, the present invention is not limited by the particular purification techniques employed to isolate the adjunct isoform or the desired protein. Many chromatography and other separation techniques are known to those skilled in the art and are applicable here.

While the present invention is not limited by the method of identifying the adjunct isoforms, identification of adjunct isoforms can be accomplished by studying the molecular weights of the desired protein and any contaminants having a molecular weight higher than the desired protein. One such method is described in Rose, et al, J. Biol. Chem. 267:19101 (1992). Contaminants having a molecular weight higher than the desired protein can be exposed to degradation conditions (e.g., extremely acid or extremely basic pH) and analyzed for degradation products. If one of these degradation products has the same mass and/or structural characteristics of the desired protein, then the contaminant can be considered an adjunct isoform having a cleavable group.

While the present invention is not limited to a particular method for converting adjunct isoforms to the desired protein, in one embodiment, a screening process can determine the proper conversion conditions. For example, one process entails a stepwise adjustment of the pH of the reaction solution to the point that the cleavable group is removed from the adjunct isoform, yet a functional or a non-irreversibly denatured desired protein results.

Moreover, the present invention is not limited by the method of chemically removing a cleavable group. In one embodiment, the group is removed or cleaved by exposing the adjunct isoform to acidic conditions (e.g., using acetic acid). In an alternative embodiment, the adjunct isoform is exposed to zinc.

The present invention is also not limited by the temperature at which the cleaving reaction is run. In general, however, the higher the temperature, the faster the adjunct isoform will be converted to the desired protein.

While chemical removal of a cleavable group may produce a protein with the same structural characteristics of the desired protein, it is sometimes necessary to oxidize reduced sulfhydryl groups to disulfide bonds. This allows the protein to attain proper folding and become a functional protein. Methods of oxidizing sulfhydryl groups are known in the art and the present invention is not limited by any particular method of oxidation.

In one embodiment, the present invention contemplates the protection of methionine groups during oxidation to prevent the formation of methionine sulfoxide. Methods for protecting methionine groups are know in the art, and the present invention is not limited by particular methods for protecting methionine groups. Methods, however, include the use of antioxidants as described by Lam, et al, J. Pharm. Sci. 86:1250 (1997) and U.S. Pat. No. 5,272,135 to Takruri.

The present invention is also not limited by the method of implementation of an oxidation reaction. For example, in one embodiment, the present invention contemplates the removal of a cleavable group followed by oxidation of sulfhydryl groups. In another embodiment, the present invention contemplates the removal of cleavable groups and oxidation of sulfhydryl groups under the same reaction conditions.

Likewise, when the chemical removal of the cleavable group and oxidation of the protein are conducted in the same reaction, the present invention is not limited by any particular method of removing cleavable groups from an adjunct isoform and oxidizing. In one embodiment, however, a screening process is conducted to determine the best conditions for chemical removal of the cleavable group. For example, experiments using a range of pH conditions can be undertaken and the amount of resulting desired protein having adequate structural integrity (i.e., not irreversibly denatured) and/or the amount of cleavable group can be measured. A plot of the amount of the desired protein having adequate structural integrity versus the reaction pH will generally result in a bell curve, with the highest point of the curve representing the ideal pH for chemical removal of the cleavable group. In such an embodiment, a similar screening can be undertaken for the oxidation reaction. If the bell curves of the chemical removal reaction and the oxidation reaction intersect, the point of intersection reveals the best pH conditions for removing the cleavable group and oxidizing the sulfhydryl groups in the same reaction. For chemical removal and oxidation of a pyruvate adjunct isoform of interferon alpha, the two curves intersect at around pH 5, revealing the best pH at which to run a combination reaction. Other reaction conditions that can be evaluated include, but are not limited to, salt concentration, temperature, etc.

After conversion of the adjunct isoforms to the desired protein, further chromatography steps may be necessary to purify the desired proteins from contaminants.

After the desired protein is suitably purified, it can be placed in a form suitable for therapeutic use, if desired. For example, when the desired protein is interferon alpha, formulations described in U.S. Pat. Nos. 4,847,079 and 4,496,537 to Kwan and U.S. Pat. No. 5,766,582 to Yuen et al. are suitable. Alternatively, other inert, pharmaceutically acceptable carriers can be either solid or liquid. Solid form preparations include powders, tablets, dispersible granules, capsules, cachets and suppositories. The powders and tablets may be comprised of from about 5 to about 95 percent desired protein. Suitable solid carriers are know in the art, e.g. magnesium carbonate, magnesium stearate, talc, sugar or lactose. Tablets, powders, cachets and capsules can be used as solid dosage forms suitable for oral administration.

For preparing suppositories, a low melting wax, such as a mixture of fatty acid glycerides (e.g., cocoa butter) is first melted, and the active ingredient is dispersed homogeneously therein by stirring. The molten homogeneous mixture is then poured into convenient sized molds, allowed to cool and thereby solidify.

Liquid form preparations include solutions, suspensions and emulsions. For example, water or water propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas.

The compounds of the present invention may also be delivered transdermally. The transdermal compositions can take the form of creams, lotions, aerosols and/or emulsions and can be included in a transdermal patch of the matrix or reservoir type as are conventional in the art for this purpose.

The quantity of active compound in a unit dose of preparation can be adjusted from about 0.01 mg to about 1000 mg, and preferably from about 0.01 mg to about 750 mg. Alternatively, the active compound can be prepared by international units, with the preferred dosages being between 3 million and 50 million international units. In such an embodiment, 3 million, 5 million, 18 million, 25 million and 50 million units dosage forms are contemplated.

Also included are solid forms which are intended to be converted, shortly before use, to liquid form preparations for either oral, topical or parenteral administrations.

The following examples serve to illustrate certain preferred embodiments and aspects of the present invention and are not to be construed as limiting the scope thereof.

EXAMPLE 1

Screening Process for Conversion of Pyruvate Adjunct Isoforms

Pyruvate adjunct isoforms can form inside cells, wherein the alpha-amino group of the N-terminal amino acid residue of a protein is condensed with the carbonyl group of pyruvate. If the pyruvate interferes with protein conformation, then only when such a pyruvate-protein adjunct isoform is hydrolyzed (pyruvate is cleaved off from a protein) can the protein freely refold into its desired form through thermodynamically favorable conformation change. If a desired protein has a disulfide bond(s), a reduced isoform resulting from the pyruvate cleavage should be oxidized as a part of refolding into a desired form.

The following procedure illustrates how to determine the optimal conditions to convert pyruvate-protein adjunct isoform into its desired form. As discussed previously, if a desired protein does not have a disulfide bond(s), screening needs to be carried out simply to maximize the pyruvate cleavage (hydrolysis). If a desired protein has a disulfide bond(s), screening needs to be performed to maximize not only pyruvate cleavage (hydrolysis) but also disulfide bond formation (oxidation).

1) Pyruvate Assay

A pyruvate assay is needed to monitor the extent of hydrolysis in order to understand pyruvate-cleavage kinetics. For example, "free" pyruvate can be quantitatively assayed by a chemical modification method or an enzymatic method. 2,4-dinitrophenylhydrazine (DNPH) can be used to derivatize pyruvate. An assay sample should be ultrafiltered in order to eliminate a pyruvate-protein adjunct isoform using a proper MWCO membrane, for example, a 10K membrane. A filtrate is incubated at acidic pH with DNPH which reacts with "free" pyruvate. DNPH-derivatized pyruvate, 2,4-dinitrophenylhydrazone, can be easily analyzed on RP-HPLC using a C8 column such as a Nucleosil C8 (5 um) column.

Since the derivatization reaction is stoichiometric, a quantitative measurement of pyruvate is also possible. An enzyme kit (e.g., lactate dehydrogenase/NADH) can also be used to measure pyruvate. This method does not require sample ultrafiltration since its mild conditions do not cleave pyruvate from a pyruvate-protein adjunct isoform during incubation.

To measure the combined amount of free pyruvate and pyruvate bound to a protein, all the bound pyruvate should be cleaved off prior to the derivatization. Since the DNPH derivatization method requires very acidic pH and relatively long incubation time, pyruvate can be cleaved off and subsequently derivatized with DNPH during the incubation. Therefore, a sample should be used without being ultrafiltered in the DNPH derivatization method in order to measure a combined amount of free and bound pyruvate in the sample.

2) Isoform Assay

At least three isoforms exist for proteins with disulfide bonds and two isoforms exist for proteins without disulfide bonds. Generally speaking, a desired protein and its reduced form can be easily resolved by RP-HPLC.

In the case of a protein having disulfide bond(s), screening will be very efficient if three isoforms (adjunct isoform, reduced and desired protein) can be quantitatively analyzed on RP-HPLC. There will be no absolute need for the pyruvate assay and it is possible to identify which step is rate-limiting, if any. However, it is usually difficult to resolve a pyruvate-protein adjunct isoform from a reduced form. In this case, a pyruvate assay is indispensable in order to optimize each conversion step.

3) Measurement of Isoform Composition

When a desired form does not have a disulfide bond(s), the isoform composition can be determined without difficulty since a pyruvate-protein adjunct isoform can be easily resolved from a desired form on RP-HPLC.

When the desired form has disulfide bond(s) and a protein adjunct isoform is not separable from its reduced form, pyruvate bound to a protein should be measured to determine isoform composition. The molar amount of pyruvate bound to a protein, which is the amount of a protein adjunct isoform, is the combined amount of free and bound pyruvate less the amount of free pyruvate. This can be measured using a sample with and without ultrafiltration in the DNPH method. Then, the amount of a reduced form is the difference between the combined amount of a protein adjunct isoform and a reduced form measured by RP-HPLC and the amount of pyruvate bound to a protein determined by a pyruvate assay. Then, the isoform composition can be calculated.

4) Screening Optimal Conditions

Whether a desired form has a disulfide bond(s) or not, the screening criteria should be the same, in order to maximize the specific rate of the conversion of the adjunct isoform into a desired form.

4.1) When a desired protein has no disulfide bond:

In this case, a desired protein forms as pyruvate is cleaved off from a pyruvate-protein adjunct isoform. Pyruvate cleavage does not have to be monitored by pyruvate assay in this case, since there is only one step, hydrolysis, involved in the conversion of the adjunct isoform into a desired form. For example, monitoring both the disappearance of the adjunct isoform and the formation of a desired form on RP-HPLC is sufficient. The incubation conditions to maximize the conversion of an adjunct isoform into a desired protein need to be found.

The first step is to investigate the reaction kinetics with respect to a working range of the protein adjunct isoform concentration to be employed in the screening. If the kinetics is first-order with respect to the adjunct isoform concentration, the sample concentration has no impact on the kinetics and any concentration can be employed during screening or parameter evaluation. Otherwise, the concentration should be kept constant during screening.

There can be many parameters which affect the hydrolysis step. The major ones could be pH, temperature, metal ions (such as zinc, ferric, ferrous, Cu, Mg, etc.), conductivity, buffers, light, and agitation. By measuring the effect of an incubation parameter on the conversion of a adjunct isoform into a desired form each parameter can be optimized. For example, several aliquots of a sample containing a pyruvate-protein adjunct isoform are incubated at a sufficient range of different pHs with all the other parameters at their respective best-guessed values. The conversion reaction in each aliquot is measured after a certain period of incubation, (e.g., overnight). The pH at which the highest conversion is obtained is determined as an optimal pH. Such an experiment is repeated to optimize other parameters with optimal values of the optimized parameters utilized instead of their previously best-guessed values. This is a typical optimization technique.

The incubation pH affects the hydrolysis rate. Generally, lower pH leads to more hydrolysis. Higher temperature also increases hydrolysis. However, hydrolysis at a very acidic pH, such as pH 2, might not work when there is irreversible precipitation of an adjunct isoform or a desired protein, or if the protein is irreversibly denatured. The presence of some metal cations can catalyze the hydrolysis. Even though a metal cation catalyzes the pyruvate cleavage, such a catalysis can be greatly metal cation concentration-dependent. Therefore, a very wide range of metal cation concentration should be employed when metal cations are screened.

There might also be interactions among parameters. For example, it might be possible that there is different optimal pH depending on whether some metal ion is present or not when such a cation has an impact on the conversion. In the case of a pyruvate adjunct isoform, the presence of Zn cation results in a different optimal pH for pyruvate cleavage (pH7.8–8.6). Therefore, it is necessary to vary at the same time not only a new parameter to be optimized but also other important parameters in order to truly optimize it.

4.2) When a desired protein has disulfide bond(s):

In a two-step conversion process, a reduced form is cleaved off from the adjunct isoform via hydrolysis and it is subsequently converted into a desired form via oxidation.

Ideally speaking, a protein adjunct isoform and a reduced form are isolated and the procedure, which is described above for the case of a protein without a disulfide bond(s), is applied to each of the adjunct isoform and the reduced form in order to optimize each step. A major difference is that oxygen transfer and some oxidants like oxidized glutathione (GS-SG) in addition to the parameters listed above can be optimized for the oxidation step. If GS-SG oxidizes only a reduced form, it will greatly enhance the oxidation or disulfide bond formation step. However, there will likely be low yield or conversion if GS-SG also oxidizes the adjunct isoform and the oxidized adjunct isoform does not easily hydrolyze. From each optimal condition, the optimal conditions for the conversion of the adjunct isoform into a desired form can be estimated. If they are reasonably close, the intermediate conditions are set as optimal conditions. Theoretically speaking, there can be different optimal conditions depending on the initial ratio of pyruvate-protein adjunct isoform to a reduced form in a sample. For example, the optimal conditions should be different when the adjunct isoform is the absolute majority than when a reduced form is the absolute majority. Therefore, it should be recognized that the sample composition should be taken into account when the optimal conditions are estimated from the individual optimal conditions for the hydrolysis and the oxidation.

Finally, the conversion optimal conditions are experimentally confirmed. It is often useful in fine-tuning the conversion optimal conditions to identify, if any, a rate-limiting step. The steady accumulation of reduced form with incubation time indicates that the oxidation step is rate-limiting. When accumulation happens, conditions more favorable to oxidation such as more oxygen, higher pH, and higher temperature should be applied to maximize the formation of the desired form. If there is always a low level of reduced protein though significant formation rate of a desired form, the cleavage step is rate-limiting. When this happens, incubation conditions can be changed so that they may improve the cleavage step, which will lead to the maximization of the formation of the desired form. If the optimal conditions for chemical removal of a cleavable group and oxidation of the protein are very far apart, they can be applied step-wise. For example, the optimal conditions for the hydrolysis step are applied first and the optimal conditions for the oxidation step are applied when the hydrolysis is almost complete.

When it is not feasible to isolate each isoform, pyruvate assay becomes indispensable, especially so when the two isoforms cannot be resolved on RP-HPLC. By monitoring pyruvate release, the hydrolysis step can be first optimized. The second step is optimized when the first step is almost over or very slow. From these optimal conditions, the overall conversion optimal conditions are estimated and experimentally confirmed. An alternative approach is that the overall conversion is optimized after the hydrolysis step is optimized. This approach might be more practical especially when it is difficult to optimize the second step due to the interference caused by significant and continuous adjunct isoform hydrolysis. As mentioned before, pH, temperature, oxygen transfer, metal cations and oxidants are important parameters to be optimized.

Interactions among parameters become more important for the two-step conversion process than they are for the one-step conversion process.

To confirm that there is no impact of such optimal condition parameters on a desired form, a desired form should be purified and its properties, including biological specific activity and purity, should be fully checked.

EXAMPLE 2

Conversion of Pyruvate Adjunct Isoform to Interferon Alpha2b

The cleavage of pyruvate and the formation of the disulfide bonds are performed at an elevated temperature (30–37° C.) and a reaction pH of 5.2–5.6. These reaction conditions are unique in that both reactions occur sequentially under the same reaction conditions and that bioactive protein is recovered.

The fractions containing the peak of protein UV-absorbance eluting from the protein isolation chromatography are pooled together and 0.45 uM filtered for sterility.

3 grams of methionine per liter of protein pool is added to the protein pool and agitated until dissolved. The pH of the pool is adjusted to 5.2–5.6 with dilute sodium hydroxide. The sodium chloride concentration is not adjusted: it is between 150–200 mM NaCl.

A stock solution consisting of 10 mM acetate pH 5.5, 200 mM methionine and 200 mM NaCl is added to the protein pool to a final concentration of 20 mM methionine.

The protein pool is transferred to a reaction vessel and the temperature is raised to 37° C. with steady agitation. The protein pool is incubated at 36–38° C. for 24–30 hours.

At the 24–30 hour time point, the reaction mixture is filtered through a depth filter, followed by a 0.45 uM filter to remove precipitates. The pool is then concentrated and diafiltered against 10 mM acetate pH 5.5 at 2–10° C.

EXAMPLE 3

Conversion of Pyruvate Adjunct Isoform to Interferon Alpha2b Using Zinc

Pyruvate adjunct isoform is converted into interferon alpha2b at 34° C. and pH 8.2 with zinc (1 M). The reaction solution is agitated during the reaction. When the conversion is about 80%, the reaction solution temperature can be decreased to 4° C. to stop the reaction.

Solution Preparation: 1M Tris Buffer: kept at 4° C., 1M Tris Base+HCl at pH 8.3, 1 mM Zn solution: kept at 4° C., 1 mM $ZnSO_4H_2O$+10 mM NaAcetate+175 mM NaCl at pH 5.5.

The fractions containing the peak of UV-absorbance eluting from the protein purification chromatography are pooled together and 0.2 uM filtered for sterility. About 0.083 (V/V) of the 1M Tris Buffer is slowly added into a protein pool (the pH of a typical protein pool is in the range of 5.2 to 5.5) which is agitated, to a pH of about 8.2.

The 1 mM Zn solution is slowly added into the basic protein pool while being agitated in order to achieve 0.6 to 1.0 molar ratio of Zn cation to total pyruvate adjunct isoform, e.g. if a pyruvate adjunct isoform concentration is 1.0 mg/mL, 30 uM of Zn or 0.03 (V/V) of the 1 mM Zn solution is needed. Use fresh Zn cation solution.

The reaction solution is heated to 34° C. in a reactor while being agitated. The reaction temperature is controlled at 34° C. throughout the reaction. Continuous agitation is also required to an extent that the mixing in the reaction solution is sufficient but not violent enough to generate bubbles. Some ventilation in the reactor should be allowed for oxygen transfer into the reaction solution. On the other hand, if the reactor is about half-fall of the reaction solution, such a ventilation is not necessary. During the reaction, a reaction sample can be taken to follow conversion using RP-HPLC. When the reaction is over, the temperature can be dropped to 4° C. for the next chromatography step.

From the above, it is clear that the present invention provides methods to identify undesirable protein isoforms, and convert them to the desired protein, which increases the overall yield and purity of the desired protein.

We claim:

1. A method for increasing the yield of an interferon alpha composition, comprising converting a pyruvate adjunct isoform of interferon alpha into interferon alpha by exposing said pyruvate adjunct isoform of interferon alpha to a solution having a pH of at least 5.0.

2. The method of claim 1, wherein said interferon alpha is interferon alpha 2b.

3. The method of claim 2, wherein said adjunct isoform is exposed to acid solution having a pH in the range of about 5.2 to about 5.6.

4. The method of claim 3, wherein said acid solution is at about pH 5.5.

5. The method of claim 4, wherein said acid solution at 34–40° C.

6. The method of claim 5, wherein said acid solution comprises an antioxidant.

7. The method of claim 6, wherein said antioxidant comprises methionine.

8. The method of claim 7, wherein said methionine is at a concentration of 5–40 mM.

9. The method of claim 1, wherein said adjunct isoform is exposed to zinc solution.

10. The method of claim 9, wherein said zinc solution is at about pH 7.8 to about pH 8.6.

11. The method of claim 10, wherein said zinc solution is at 30–38° C.

12. The method of claim 11, wherein said zinc solution comprises an antioxidant.

13. The method of claim 12, wherein said antioxidant comprises methionine.

14. The method of claim 13, wherein said methionine is at a concentration of 5–40 mM.

15. The method of claim 3, wherein said is exposed to said solution for 24–30 hours.

16. The method of claim 11, wherein the ratio of said Zinc to said isoform is 0.6 to 1.0.

17. The method of claim 16, wherein said isoform is exposed to said solution until 80% of said isoform is converted to interferon alpha.

* * * * *

UNITED STATES PATENT AND TRADEMARK OFFICE
CERTIFICATE OF CORRECTION

PATENT NO. : 6,281,337 B1
DATED : November 12, 1999
INVENTOR(S) : Cannon-Carlson et al.

It is certified that error appears in the above-identified patent and that said Letters Patent is hereby corrected as shown below:

Column 10,
Line 20, change "solution at" to read -- solution is at --.
Line 40, change "said is" to read -- said isoform is --.

Signed and Sealed this

Thirteenth Day of August, 2002

*Attest:*

*Attesting Officer*

JAMES E. ROGAN
*Director of the United States Patent and Trademark Office*